(12) United States Patent
Zhdanov

(10) Patent No.: US 6,876,878 B2
(45) Date of Patent: *Apr. 5, 2005

(54) MEDICAL BROAD BAND ELECTROMAGNETIC HOLOGRAPHIC IMAGING

(75) Inventor: Michael S. Zhdanov, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 379 days.

This patent is subject to a terminal disclaimer.

(21) Appl. No.: 09/876,262

(22) Filed: Jun. 6, 2001

(65) Prior Publication Data

US 2002/0062074 A1 May 23, 2002

Related U.S. Application Data

(63) Continuation of application No. 09/214,217, filed as application No. PCT/US97/11217 on Jun. 26, 1997, now Pat. No. 6,253,100
(60) Provisional application No. 60/020,622, filed on Jun. 26, 1996.

(51) Int. Cl.[7] ............................................... A61B 5/00
(52) U.S. Cl. ...................................... 600/407; 600/547
(58) Field of Search ................................ 600/407, 430, 600/547, 425; 324/600, 637, 693, 638, 639; 342/22

(56) References Cited

U.S. PATENT DOCUMENTS

| | | | |
|---|---|---|---|
| 3,887,923 A | | 6/1975 | Hendriz |
| 3,953,822 A | * | 4/1976 | Vilkomerson ............... 367/11 |
| 4,852,575 A | | 8/1989 | Nikoonahad |
| 4,945,239 A | | 7/1990 | Wist et al. |
| 4,948,974 A | | 8/1990 | Nelson et al. |
| 4,961,428 A | * | 10/1990 | Nikias et al. ............... 600/512 |
| 5,072,128 A | | 12/1991 | Hayano et al. |
| 5,303,710 A | | 4/1994 | Bashkansky et al. |
| 5,327,139 A | | 7/1994 | Johnson |
| 5,373,443 A | | 12/1994 | Lee et al. |
| 5,413,098 A | | 5/1995 | Benaron |
| 5,418,797 A | | 5/1995 | Bashkansky et al. |
| 5,435,312 A | * | 7/1995 | Spivey et al. ............... 600/448 |
| 5,476,108 A | | 12/1995 | Dominguez et al. |
| 5,503,150 A | | 4/1996 | Evans |
| 5,588,032 A | * | 12/1996 | Johnson et al. ................ 378/8 |
| 5,592,170 A | | 1/1997 | Price et al. |
| 5,606,969 A | | 3/1997 | Butler et al. |
| 5,673,050 A | | 9/1997 | Moussally et al. |
| 5,715,819 A | * | 2/1998 | Svenson et al. ............. 600/425 |
| 5,807,257 A | | 9/1998 | Bridges |
| 5,841,288 A | * | 11/1998 | Meaney et al. ............. 324/639 |
| 6,253,100 B1 | * | 6/2001 | Zhdanov ..................... 600/407 |

* cited by examiner

Primary Examiner—Ruth S. Smith
(74) Attorney, Agent, or Firm—Knobbe, Martens, Olson & Bear, LLP

(57) ABSTRACT

A method of imaging an object, such as a diseased human heart or bone or malignant tumor, in a nontransparent medium, such as the human body, involves placing an array of transmitters and receivers in operational association with the medium. The transmitters generate a broad band harmonic (frequency domain) or pulse (time domain) primary electromagnetic field (EM) field, including the lower frequency portions of the EM spectrum, whose propagation is typically characterized by the diffusion phenomena, or by the combination of the diffusion and wave phenomena. The primary field propagates through the examined medium and interacts with the object to produce a scattered field, which is recorded by the receivers. The scattered EM field components measured by the receivers are applied as an artificial EM field to generate a backscattering EM field. Cross power spectra of the primary and backscattering fields (in the frequency domain) or cross correlation between these fields (in the time domain) produce a numerical reconstruction of an EM hologram. The desired properties of the medium, such as conductivity or dielectric permittivity, are then derived from this hologram.

17 Claims, 5 Drawing Sheets

MEDICAL BROAD BAND ELECTROMAGNETIC HOLOGRAPHIC IMAGING

This application is a continuation application of U.S. application Ser. No. 09/214,217, filed Dec. 23, 1998, now U.S. Pat. No. 6,253,100 issued Jun. 26, 2001, which claims priority from PCT application PCT/US97/11217, filed Jun. 26, 1997, which claims priority from U.S. Provisional Application Ser. No. 60/020,622, filed Jun. 26, 1996, entitled "METHOD OF BROAD BAND ELECTROMAGNETIC HOLOGRAPHIC IMAGING."

FIELD OF THE INVENTION

This invention relates to three dimensional ("holographic") imaging. It is specifically directed to the electromagnetic (EM) imaging of an object within a nontransparent medium. It provides methodology and apparatus for conducting nondestructive and/or non-invasive inspections, utilizing broad band electromagnetic signals.

BACKGROUND OF THE INVENTION

Conventional optical holography constructs a volume (three dimensional) image of an object by displaying the amplitude and the phase structure of a wavefront of light. A reference wave of light is relied upon to facilitate the recording of both the amplitude and the phase condition of the object light by means of photographic emulsion. This reference wave is coherent with the object light and interferes with it, producing diffraction patterns which form an optical hologram on the photographic emulsion. To generate a volume image, this optical hologram need merely be illuminated with a reference light wave. The resulting diffraction pattern wave (as scattered by the emulsion) is identical to the original wavefront of light scattered by the object, and therefore reproduces the volume image of the object.

U.S. Pat. No. 3,887,923 to Hendrix discloses an application of the principles of optical holography within the radio-frequency domain. The '923 patent discloses a passive radio direction finder which monitors the amplitude and phase of radio-frequency wave fronts across an aperture. An array of antennas sample the phase of incoming wave fronts. Each antenna is associated with a mixer, and one of the antennas provides a mixer reference signal for an input to each mixer. The signals are processed through an analog-to-digital converter and a computer programmed rapidly to execute Fourier transforms, eventually to produce a numerical reconstruction of the radio frequency hologram.

U.S. Pat. No. 5,299,033 to Leith, et al discloses a method whereby an image of an object embedded in a diffusing medium is formed by propagating a coherent light pulse through the diffusing medium and applying a reference pulse to gate precisely the first emerging light transmitted through the diffusing medium. To produce an image, it is necessary for the diffusing medium to be transparent, because the method relies upon optical light.

There have been several attempts to develop an imaging method, utilizing a low frequency electromagnetic (EM) field, especially as applied to the solution of geophysical problems. K. H. Lee and G. Xie, in both U.S. Pat. No. 5,373,443 and the article, "A new approach to imaging with low-frequency electromagnetic fields," Geophysics, volume 58, pages 780–796 (1993), describe a method for imaging electrical conductivity with low-frequency electromagnetic fields, using wavefield transforms and ray tomography. This work has recognized a relationship between low frequency diffusion EM field equations and wave equations, but practical applications of this method have been directed to defining interfaces, rather than three dimensional imaging.

In the article entitled "Continuation of the transient electromagnetic field in the geoelectrical problems," Physics of the Earth (Izvestia Akademy Nauk—in Russian), No. 12, pages 60–69, 1981, the present inventor presented a mathematical transform, based upon the theory of Stratton-Chu integrals, of the field recorded on the earth's surface and scattered from a subsurface geological object downward to locate and image the object. Subsequently, the present inventor and M. A. Frenkel coauthored an article entitled "The solution of the inverse problems on the basis of the analytical continuation of the transient electromagnetic field in reverse time," J. Geomagn. Geolelectr., volume 35, pages 747–765 (1983), which developed this method and introduced an imaging concept based upon downward extrapolation of an EM field in reverse time (electromagnetic migration).

The inventor has further coauthored the articles: "Resistivity Imaging by Time Domain Electromagnetic Migration (TDEMM)" (with P. Traynin and O. Portniaguine), Exploration Geophysics, volume 26, pages 186–194 (1995), reporting work which tested the imaging concept using controlled-source electromagnetic data, with limited success for two-dimensional models only, and "Underground Imaging by Frequency Domain Electromagnetic Migration," (with P. Traynin and J. R. Booker), Geophysics, volume 61, No. 3, pages 666–682 (1996), explaining application of the migration method to natural EM field geophysical data interpretation, but this study was limited to two-dimensional magnetotelluric problems.

These earlier efforts to develop a method for quickly interpreting geophysical EM data over two-dimensional geoelectrical structures have met with limited success. Moreover, they have not pointed towards a practically useful method for accomplishing broad band EM imaging of three-dimensional objects in nontransparent media. There remains a need for a method of imaging capable of providing the volume image of objects located in nontransparent media similar to images produced by optical or radio-wave holography. Such a method would be useful in geophysical exploration, in environmental study (for example, in searching for buried mines), for nondestructive detection of defects in metal and in medical applications (for example, in breast cancer or diseased bone diagnoses).

SUMMARY OF THE INVENTION

A broad band electromagnetic (EM) field is utilized for imaging an object located in a nontransparent medium. Examples of a nontransparent medium are geophysical structures of the earth, animal (including human) bodies and substances generally which block transmissions from the high frequency range of the electromagnetic spectrum. By utilizing the lower frequency portions of the EM spectrum, useful images can be obtained under circumstances in which neither optical nor radio-frequency signals can propagate through the medium in which the image target is located. Lower frequency waves characteristically propagate deeper through any diffusing medium. The propagation of a lower frequency EM field is typically characterized by the diffusion phenomena, or by a combination of the diffusion and wave phenomena. The characteristics of propagation are related to the frequency of the electromagnetic field as well as the conductivity/permittivity of the medium. For example, an EM field of approximately one megahertz or less may cause a propagation characterized by diffusion phenomena in one medium, and an EM field of approximately ten megahertz or less may cause a propagation characterized by a combination of diffusion and wave phenomena in one medium.

In practice, the EM transmitting/receiving system may be placed in operable association with the surface of the examined medium. "Operational association," in this context, means any location which facilitates propagation of a field through an examined medium from a transmitter to a receiver. Ordinarily, the transmitters and receivers are most conveniently positioned directly on the surface of the examined medium, but they can be positioned within the medium or, in some instances, inductor devices may be placed in the proximity of the medium. The transmitters and receivers may be either galvanic or inductive in construction. Transmitters and receivers of both types may be used in specific applications.

The transmitters generate a harmonic (frequency domain) or pulse (time domain) primary EM field which propagates through the medium containing the target object, and is recorded by the receivers. A reference signal is provided to measure relative phases in the frequency domain. The recorded amplitudes and phases of the electromagnetic field scattered by the object form a broad band EM hologram. The volume image of the object can be reconstructed by "illuminating" the broad band EM hologram with the reference signal. Unlike optical or radio-frequency holographic imaging techniques, which can yield a visible image optically, reconstruction in accordance with this description is done numerically, using computer transformation techniques.

A new capability is provided for imaging in nontransparent media with a broad band EM field. The EM transmitting/receiving system is generally placed on the surface of the examined medium. The transmitters generate either (or both) a harmonic (frequency domain) or pulse (time domain) primary EM field which propagates through the medium containing the object. The "scattered-by-the-object" EM field is recorded by the receivers. A central processing unit (CPU) is connected to collect the recorded amplitudes and phases of scattered-by-the-object electromagnetic field and to form a broad band EM hologram.

The method is ideally suited for applications which determine the distribution of electromagnetic parameters (such as conductivity or dielectric permittivity distribution) within a target object or substance with high accuracy and resolution. The desired properties, such as conductivity or dielectric permittivity, of the target are readily derived from the hologram. The measured EM field components in the receiver locations (amplitudes and phases in frequency domain or time signals in time domain) are conveniently selected as the boundary conditions of the EM field to generate numerically the backscattering EM field. Vector cross power spectra of the primary and backscattering fields produce a numerical reconstruction of a volume image of conductivity or dielectric permittivity distribution.

An imaging apparatus, capable of performing in real time in accordance with the described method for broad band EM holographic imaging requires a relatively simple hardware arrangement and simple software.

The application describes a method of imaging an object, such as a diseased human organ or bones, in a nontransparent medium, such as the human body. The method involves placing an array of transmitters and receivers in operational association with the medium. The transmitters generate a harmonic (frequency domain) and/or a pulse (time domain) primary EM field which propagates through the medium The primary field interacts with the object to produce a scattered field, which is recorded by the receivers. The scattered EM field components measured by the receivers are applied as an artificial EM field to generate a backscattering EM field. This backscattered field may be obtained empirically or by numerical calculation. Cross power spectra of the primary and backscattering fields (in frequency domain) or cross correlation between these fields (in time domain) produce a numerical reconstruction of an EM hologram. The desired properties of the medium, such as conductivity or dielectric permittivity, may then be derived from this hologram.

More specifically, an anomalous target located in a nontransparent examined medium may be located and characterized through a method comprising the steps of:

a. placing an electromagnetic transmitter source in transmission contact with the examined medium;

b. placing electromagnetic receivers at various receiving positions with respect to the examined medium, spaced from the transmitter source;

c. operating the transmitter source to generate a broad band electromagnetic field, comprising an harmonic (frequency domain) and/or pulse (time domain) electromagnetic field, whereby the generated electromagnetic field propagates through the examined medium to interact with the target, resulting in a scattered electromagnetic field;

d. measuring the scattered electromagnetic field with the receivers;

e. obtaining a background field $\{E^b, H^b\}$ representative of the examined medium without the presence of the anomalous target (often referred to as the "background" medium);

f. obtaining a backscattering anomalous field $\{E^{as}, H^{as}\}$ equivalent to that obtainable by illuminating the background medium with the scattered electromagnetic field transmitted from the positions of the receivers; and g. producing a broad band holographic image of the anomalous target by calculating cross power spectra of the background and the backscattering fields (frequency domain) and/or cross correlation functions between the background and the backscattering fields (time domain).

Ideally, the scattered electromagnetic field measured by step d. is input to a computer and the computer is operated to: (1) analyze the scattered electromagnetic field; (2) numerically simulate illumination of the background medium by the original transmitter source; (3) compute the backscattering anomalous field $\{E^{as}, H^{as}\}$ by simulating illumination of the background medium from the locations of the receivers with electric and magnetic currents equivalent to those of the scattered electromagnetic field; and (4) constructing a volume image of electrical conductivity and/or dielectric permittivity by calculating cross power spectra of the background and backscattering fields.

As applied to imaging an anomalous region located within an organism, such as the bones, liver, heart, or malignant tumor in some organ of a human being, the method may comprise the steps of:

a. placing an electromagnetic transmitter source on the surface of the organism (or optionally, in the case of inductor devices, in the proximity of the organism);

b. placing electromagnetic receivers at various positions on the surface of the organism (or optionally, in the case of inductor devices, in the proximity of the organism), spaced from the transmitter source;

c. operating the transmitter source to generate a broad band electromagnetic field comprising an harmonic (frequency domain) and/or pulse (time domain) electromagnetic field, whereby the generated electromagnetic field propagates through the organism to interact with the anomalous region, resulting in a scattered electromagnetic field;

d. measuring the scattered electromagnetic field with the receivers;

e. obtaining a background field $\{E^b, H^b\}$ representative of the organism without the presence of the anomalous region (often referred to as a "reference" organism, equivalent to a "background medium");

f. obtaining a backscattering anomalous field $\{E^{as}, H^{as}\}$ equivalent to that obtained by illuminating the reference organism by transmitting the scattered electromagnetic field from the positions of the receivers; and g. producing a broad band holographic image of the anomalous region by calculating cross power spectra of the background and the backscattering fields or cross correlation functions between the background and the backscattering fields.

BRIEF DESCRIPTION OF THE DRAWINGS

In the drawings, which illustrate one embodiment of carrying out the invention.

DETAILED DESCRIPTION OF THE PREFERRED EMBODIMENT

Figure 1:
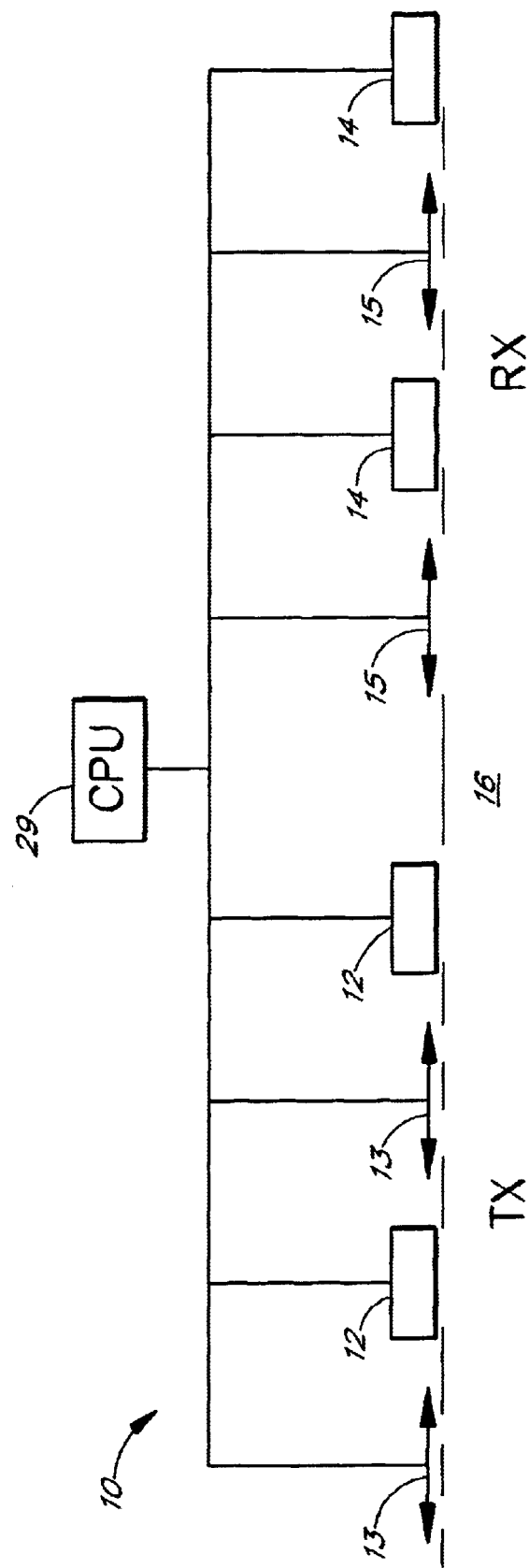
FIG. 1 illustrates an EM transmitting/receiving system placed on the surface of an examined medium.

A presently preferred approach to broad band EM holography is illustrated by FIG. 1. As illustrated, the imaging system 10 includes induction 12 or galvanic 13 EM field transmitters and induction 14 or galvanic 15 EM field receivers placed on the surface of the examined medium 16 (FIG. 1). The array of receivers 14, 15 may either be one-dimensional (as shown) or two-dimensional (typically, distributed in a grid pattern across the surface of observation). Transmitters 12, 13 (or a single transmitter) can be located arbitrarily on the surface of the examined medium 16.

Figure 3:
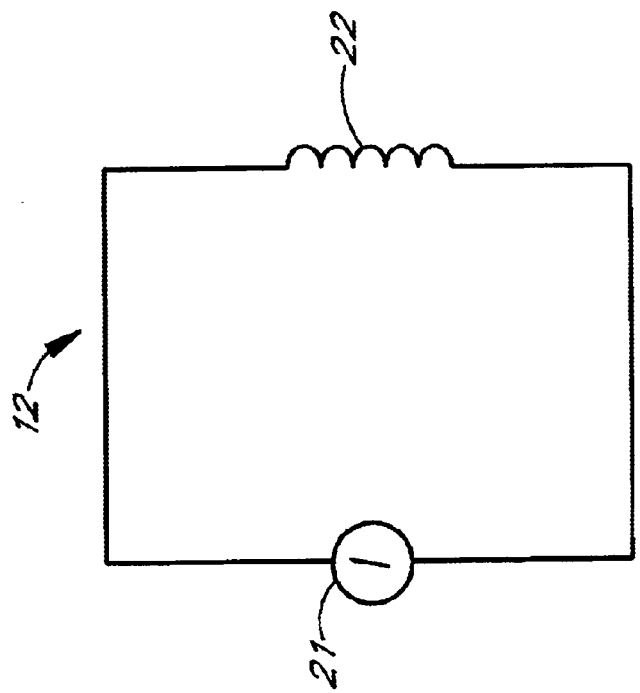
FIG. 3 is a simplified diagram of an induction transmitter useful in the system of FIG. 1.
Figure 2:
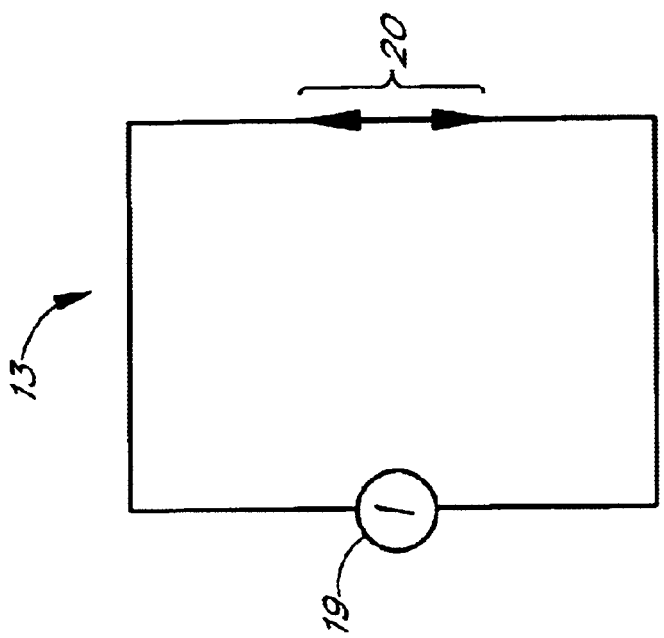
FIG. 2 is a simplified diagram of a galvanic transmitter useful in the system of FIG. 1.
Figure 4:
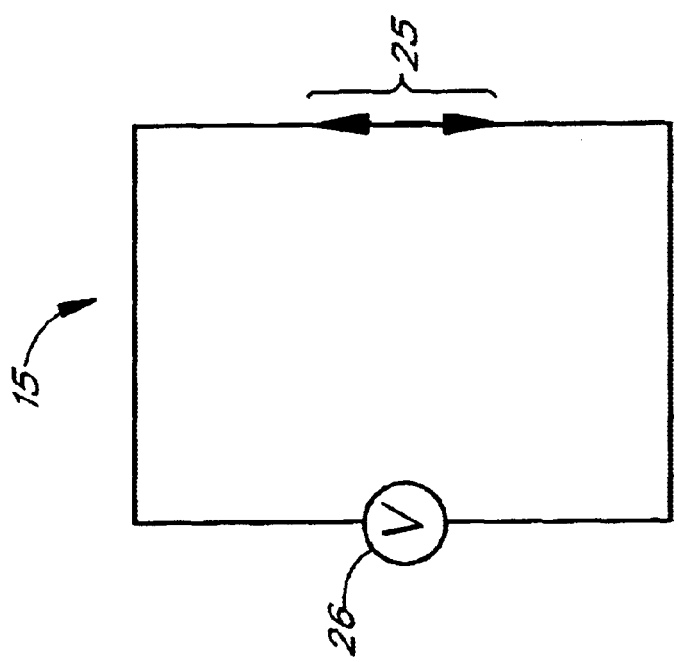
FIG. 4 is a simplified diagram of a galvanic receiver useful in the system of FIG. 1.

The galvanic transmitter 13 (FIG. 2) includes the transient current source 19 connected across the pair of current electrodes 20. The induction transmitter 12 (FIG. 3) includes the transient current source 21 connected across a solenoid coil 22. The galvanic receiver 15 (FIG. 4) includes a pair of receiver electrodes 25 connected across the voltmeter 26.

Figure 5:
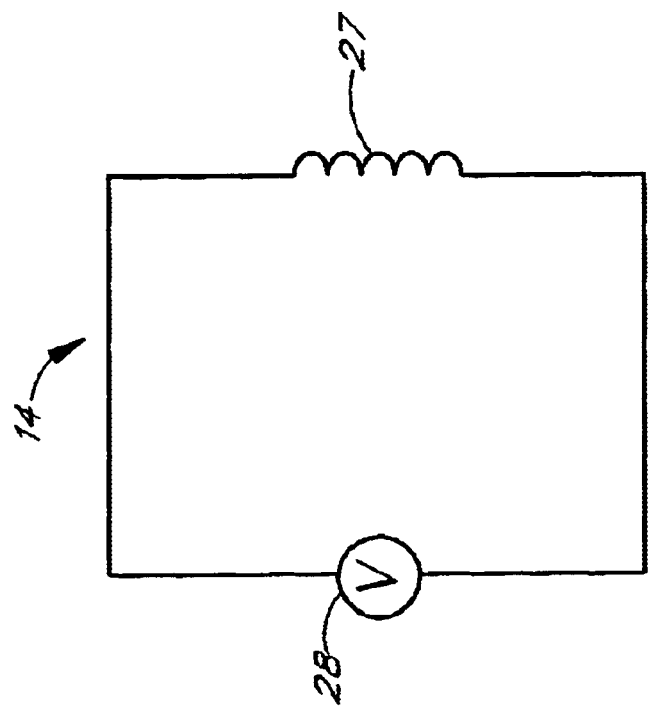
FIG. 5 is a simplified diagram of an induction receiver useful in the system of FIG. 1.

The induction receiver 14 (FIG. 5) includes a solenoid coil 27 connected across the voltmeter 28. In use, galvanic devices are positioned in direct contact with the examined medium, but induction devices are operable from positions in the proximity of, but not necessarily in contact with, the examined medium.

Figure 6:
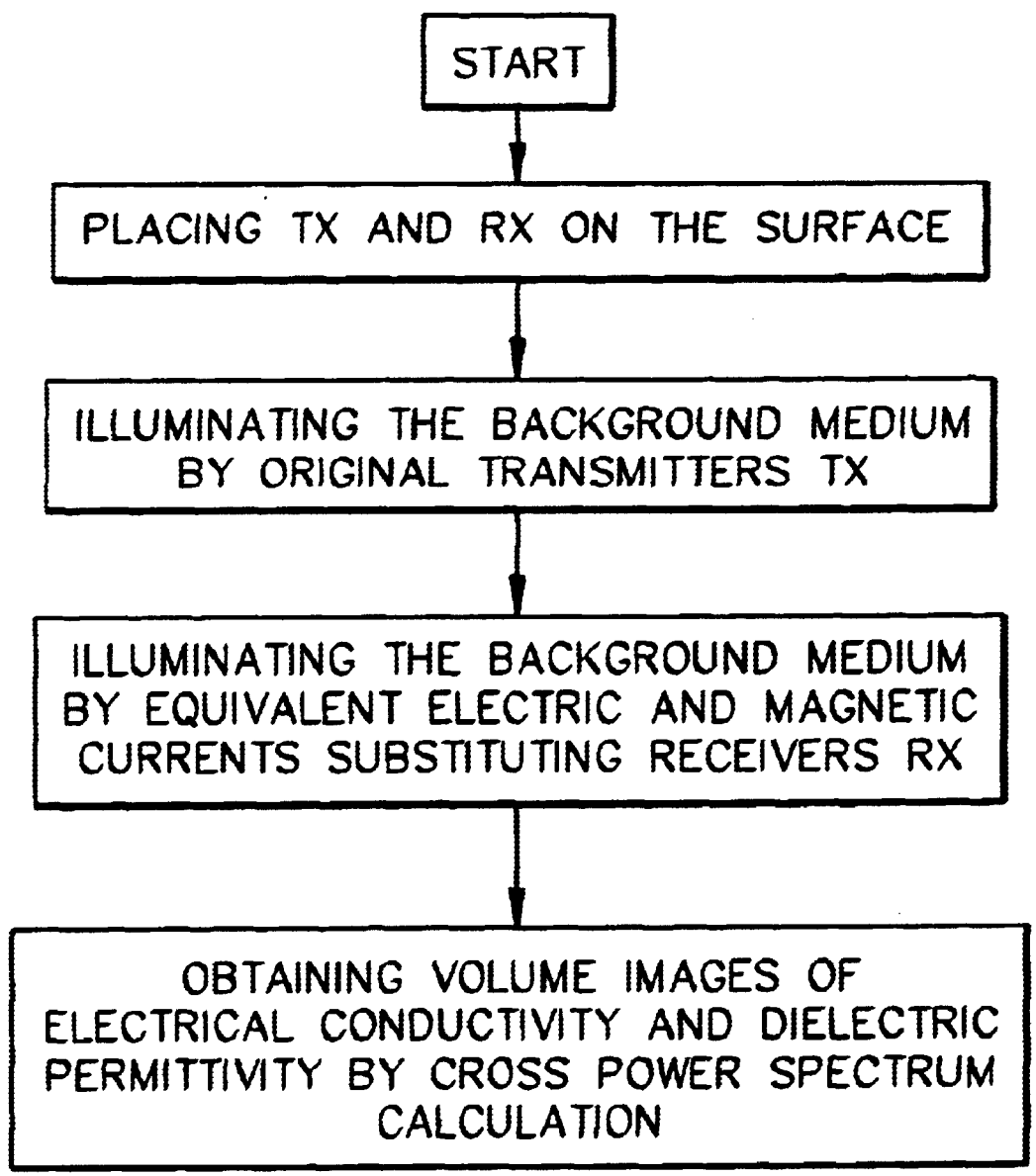
FIG. 6 is a flow chart illustrating a method of holographic imaging by the broad band EM system of FIG. 1.

The central processing unit 29 (FIG. 1) operates the broad band EM holographic imaging system, as it is schematically shown by FIG. 6. The incoming EM field generated by a transmitter (or, as illustrated, an array TX of transmitters) is received by an array of receivers RX, and is recorded by the central processing unit 29. In the output of the receiver array shown in FIG. 1, the EM field measurements are inherently reduced to numerical values. It is thus expedient to proceed with a numerical reconstruction of the volume image.

EXAMPLE 1

The following explanation of the principles of broad band EM holographic imaging reconstruction is offered to assist those skilled in the art to practice the invention. It is not intended thereby to limit the scope of the invention to any particular theory of operation or to any field of application.

A three dimensional inhomogeneous medium, with a known background complex conductivity, $\tilde{\sigma}_b$, contains a local inhomogeneous object D with an arbitrarily varying complex conductivity $\tilde{\sigma}=\tilde{\sigma}_b+\tilde{\sigma}_a$. The location of D and its anomalous conductivity $\tilde{\sigma}_a$, are unknown. The examined medium is considered to be non-magnetic, and hence $\mu=\mu_0=4\pi\times10^{-7}$ H/m, where $\mu$ is the magnetic permeability and $\mu_0$ is the free-space magnetic permeability. The model is excited by an EM field generated by a given system of sources (transmitters TX) with an electric current density $j^e$. This field is time harmonic as $e^{-i\omega t}$ and is observed by the system of receivers RX located on the surface S of the examined medium. Complex conductivity includes the effect of displacement currents: $\tilde{\sigma}=\sigma-i\omega\epsilon$, where $\sigma$ and $\epsilon$ are electrical conductivity and dielectric permittivity. The total EM field observed in this model can be represented as a sum of background (normal) field $\{E^b, H^b\}$ generated by the given system of transmitters in the model with the background conductivity distribution, and an anomalous field $\{E^a, H^a\}$, due to an inhomogeneity $\tilde{\sigma}_a(r)$:

$$E=E^b+E^a, H=H^b+H^a \tag{1}$$

where r is the radius vector of the observation point.

To generate the volume image of the object within the inhomogeneous medium, the same transmitter/receiver system is re-deployed in the same spatial configuration as used for the receiving mode of operation, on the surface of the medium with the conductivity equal to the background conductivity $\tilde{\sigma}_b$ (background medium). The receivers are operated as (or replaced by) auxiliary transmitters which generate electric $j_s^e$ and magnetic $j_s^m$ currents equivalents to those evaluated from the anomalous field previously recorded by the receivers, located on the surface S:

$$j_s^e=-n\times H^{a*},$$
$$j_s^m=n\times E^{a*}, \tag{2}$$

where n is the unit vector of normal to S pointing outward the examining medium, and * indicates a complex conjugate value.

A typical imaging process thus comprises:

1. Illuminating the background medium by a selected system of transmitters (background field $\{E^b, H^b\}$ generation).
2. Illuminating the background medium by artificial transmitters located in the positions of the receivers and operated in response to equivalent (fictitious) electric $j_s^e$ and magnetic $j_s^m$ currents, determined by formulae (2) (backscattering anomalous field $\{E^{as}, H^{as}\}$ generation).
3. Producing a broad band holographic image by calculating cross power spectra of the background and backscattering fields.

Referring to FIGS. 1 and 6, the operation of imaging system 10 can be summarized as follows: An electromagnetic signal is generated by transmitters 12, 13, and is recorded by receivers 14, 15, placed on the surface of an examined medium, (for example, the earth or the body of a human being). The CPU system 29 analyzes the recorded field and fulfills the following numerical processes:

(1) It numerically stimulates illumination of the background medium by the original system of transmitters TX.
(2) It computes the backscattering anomalous field $\{E^{as}, H^{as}\}$, simulating illumination of the background medium by equivalent electric and magnetic currents, substituting the receivers RX.
(3) It constructs the volume images of electrical conductivity and dielectric permittivity by calculating cross power spectra of the background and backscattering fields.

EXAMPLE 2

The image generating method solves the minimum energy flow problem for the residual field $\{E^\Delta, H^\Delta\}$ computed as the difference between the observed field $\{E_{obs}, H_{obs}\}$ and numerically calculated (predicted) field $\{E_{pr}, H_{pr}\}$ for a constructed image.

The energy flow of the residual electromagnetic field can be calculated using the complex Poynting vector P, introduced by the formula:

$$P = \frac{1}{2} E^\Delta \times H^{\Delta^*}. \tag{3}$$

which is known to be a non-negative function.

The measure $\Phi$ of the difference between the observed and predicted fields can be introduced as the energy flow of the residual field through the surfaces of observations, integrated over the frequency $\omega$:

The theoretical predicted fields $E_{pr}(r, \omega)$, $H_{pr}(r, \omega)$ depend on the sum of the background $\tilde{\sigma}_b(r)$ and anomalous conductivity distribution $\tilde{\sigma}_a(r)$ in the examined $$\Phi = \tag{4}$$

$$Re \int_\Omega \int\!\!\int_S P \cdot n \, ds d\omega = \frac{1}{2} Re \int_\Omega \int\!\!\int_S [E^\Delta(r,\omega) \times H^{\Delta^*}(r,\omega)] \cdot n ds d\omega$$

medium, and, therefore, the residual field energy flow $\phi$ is a function of $[\tilde{\sigma}_b(r) + \tilde{\sigma}_a(r)]$:

$$\phi = \phi[\tilde{\sigma}_b + \tilde{\sigma}_a]. \tag{5}$$

It can be expressed approximately as:

$$\phi[\tilde{\sigma}_b + \tilde{\sigma}_a] \approx \phi(\tilde{\sigma}_b) + \delta\phi(\tilde{\sigma}_b, \tilde{\sigma}_a) \tag{6}$$

where $\delta\phi(\tilde{\sigma}_b, \tilde{\sigma}_a)$ is a gradient of the residual field energy flow. It is a linear function of anomalous conductivity and is computed by the formula:

$$\delta\phi(\tilde{\sigma}_b, \tilde{\sigma}_a) = \tag{7}$$

$$-\frac{1}{2} Re \int\!\!\int\!\!\int_D \int_\Omega \tilde{\sigma}_a(r') \int\!\!\int_S n \cdot \{E^{a^*}(r, \omega) \times \hat{G}_H^b(r \mid r', \omega) -$$

$$H^{a^*}(r, \omega) \times \hat{G}_E^b(r \mid r', \omega)\} ds \cdot E^b(r', \omega) d\omega dv',$$

where v is the volume and dv is the elemental volume of integration and where $\hat{G}_E^b$ and $\hat{G}_H^b$ are electric and magnetic Green's tensors for the background conductivity $\tilde{\sigma}_b(r)$, whose vector components relate the electric and magnetic fields excited at the point r by an electric dipole source of unit intensity located at the point r' of the domain D.

It is known from the literature that the integral over the surface of observation can be treated as the backscattering anomalous electric field $E^{as}(r',\omega)$:

$$E^{as}(r', \omega) = \int\!\!\int_S \{j_s^m$$

$$(r, \omega) \cdot \hat{G}_H^b(r|r',$$

$$\omega) + j_s^e(r, \omega) \cdot \hat{G}_E^b$$

$$(r|r', \omega)\} ds = \int\!\!\int_S r \cdot \{E^a$$

$$^*(r,\omega) \times \hat{G}_H^b$$

$$(r|r', \omega) - H^{a*}(r, \omega)$$

$$\times \hat{G}_E^b(r|r', \omega)\} ds. \tag{8}$$

Therefore, in accordance with the equations (7) and (8) and the formula $\tilde{\sigma}_a(r') = \sigma_a(r') - i\omega\epsilon_a(r')$, the gradient of the residual field energy flow becomes:

$$\delta\phi(\tilde{\sigma}_b, \tilde{\sigma}_a) = \tag{9}$$

$$-\frac{1}{2} Re \int\!\!\int\!\!\int_D \int_\Omega [\sigma_a(r') - i\omega\epsilon_a(r')] E^b(r', \omega) \cdot E^{as}(r', \omega) d\omega dv' =$$

$$-\frac{1}{2} \int\!\!\int\!\!\int_D \sigma_a(r') A(r') dv' - \frac{1}{2} \int\!\!\int\!\!\int_D \epsilon_a(r') B(r') dv',$$

where A(r) is a cross power spectrum of background and backscattering fields, computed by the formula:

$$A(r) \approx Re \int_\Omega E^b(r, \omega) \cdot E^{as}(r, \omega) d\omega, \tag{10}$$

B(r) is a cross power spectrum of the time derivative of the background field and backscattering fields, computed by the formula:

$$B(r) \approx Re \int_\Omega (-i\omega) E^b(r, \omega) \cdot E^{as}(r, \omega) d\omega, \tag{11}$$

and $\Omega$ is the frequency range.

Equation (9) provides a choice of selecting $\sigma_a(r')$ minimizing $\phi$:

$$\tilde{\sigma}_1(r') = \sigma_a(r') - i\omega\epsilon_a(r') = kA(r') - i\omega kB(r'), \tag{12}$$

taking into account, that:

$$\phi(\tilde{\sigma}_b + \tilde{\sigma}_a) = \phi(\tilde{\sigma}_b + kA - i\omega kB) \approx \phi(\tilde{\sigma}_b(r)) + k\delta\phi(\tilde{\sigma}_b, A - i\omega B) = \quad (13)$$

$$\phi(\tilde{\sigma}_b) - \frac{1}{2}k\iiint_D |A(r')|^2 dv' - \frac{1}{2}k\iiint_D |B(r')|^2 dv' < \phi(\tilde{\sigma}_b),$$

where k>0 is a scale factor determined numerically by a linear search for the minimum of the functional:

$$\phi(\tilde{\sigma}_b + \tilde{\sigma}_a) = \phi(\tilde{\sigma}_b + kA - i\omega kB) = \phi(k) = \min. \quad (14)$$

Hence, one of the important features is the ability to produce anomalous electrical conductivity and dielectric permittivity of the target which minimize the residual field energy flow through the receivers. Generally, this approach is referred to as the inverse problem solution, because the residual field is the difference between the observed data and numerically predicted data, and the goal is to determine the parameters (material properties and location) of the target. The present method resolves this inverse problem in a new way by minimizing the residual field flow. It is realized numerically through the following three steps:

Step 1. Calculating the background field $\{E^b, H^b\}$ by numerically solving the equations:

$$\nabla \times H^b = \tilde{\sigma}_b E^b + j^e,$$

$$\nabla \times E^b = i\omega\mu H^b, \quad (15)$$

assuming that the sources $j^e$ and background conductivity $\tilde{\sigma}_b$ are known. The numerical methods of solving this problem are well developed. (See Zhdanov M. S. and G. V. Keller "The geo electrical methods in geophysical exploration," Elsevier, 1994). The calculations are simplified in the case of homogenous or one dimensional background conductivity $\tilde{\sigma}_b$.

Step 2. Calculating the backscattering anomalous field $\{E^{as}, H^{as}\}$, by numerically solving the equations:

$$\nabla \times H^{as} = \tilde{\sigma}_b E^{as} + j_S^e,$$

$$\nabla \times E^{as} = i\omega\mu H^{as} - j_S^m, \quad (16)$$

assuming that the sources $j_S^e$ and $j_S^m$ and background conductivity $\tilde{\sigma}_b$ are known. In particular, equation (16) can be solved using integral formula (8), which actually solves the boundary value problem for backscattering an anomalous field. The numerical methods of calculating electric and magnetic Green's tensors $\hat{G}_E^b$ and $\hat{G}_H^b$ for one dimensional background conductivity $\tilde{\sigma}_b(r)$ are also well developed. (See Zhdanov, M. S., Integral transforms in geophysics, Springer-Verlag, 1988.) In particular, for homogenous background conductivity, the Green's tensors can be determined by the formulae:

$$\hat{G}_E^b = \left(\hat{I} + \frac{1}{i\omega\mu\tilde{\sigma}_b}\nabla\nabla\right)G^b, \hat{G}_E^b = \frac{1}{i\omega\mu}\nabla \times \hat{I}G^b, \quad (17)$$

where $\hat{I}$ is a unit tensor and $G^b$ is a scalar Green's function for the Helmholtz equation, calculating by the expression:

$$G^b = G^b(r | r', \omega) = -\frac{\exp\left[-(1-i)\sqrt{\omega\mu\tilde{\sigma}_b/2}\,|r-r'|\right]}{4\pi|r-r'|}. \quad (18)$$

Numerical algorithm for backscattering anomalous field reconstruction is given by the formula deriving from equation (8):

$$E^{as}(r', \omega) = \Sigma_{j=1}^N n(r_j) \cdot \{E^{a*}(r_j, \omega) \times \hat{G}_H^b(r_j|r', \omega) - H^{a*}(r_j, \omega) \times \hat{G}_E^b(r_j|r', \omega)\}\Delta S_j. \quad (19)$$

In the case when transmitters generating a pulse (time domain) background EM field which propagates through the medium containing the object, the calculation of the backscattering field in time domain can be fulfilled by the formula (see Zhdanov, M. S., Integral transforms in geophysics, Springer-Verlag, 1988):

$$E^{as}(r', -t') = \int_T \iint_S n \cdot \{E^a(r, t) \times \hat{G}_H^b(r, t|r', t') - H^a(r, t) \times \hat{G}_E^b(r, t|r', t')\}dsdt. \quad (20)$$

The corresponding numerical formula in time domain has the form:

$$E^{as}(r', -t') = \Sigma_{l=1}^L$$

$$\Sigma_{j=1}^N n(r_j) \cdot \{E^a$$

$$(r_j, t_l) \times \hat{G}_H^b$$

$$(r_j, t_l|r', t') - H^a$$

$$(r_j, t_l) \times \hat{G}_E^b$$

$$(r_j, t_l|r',$$

$$t')\}\Delta S_j \Delta t_l. \quad (21)$$

Step 3. Constructing the volume images of anomalous conductivity $\sigma_a$ and of anomalous permittivity $\epsilon_a$ distributions (the broad band EM holographic images) by calculating cross power spectrum $A(r)$ of background and backscattering fields and cross power spectrum $B(r)$ of the time derivative of the background field and backscattering field:

$$\sigma_a(r) \approx k A(r) = k Re \Sigma_{m=1}^M E^b(r, \omega_m) \cdot E^{as}(r, \omega_m) \Delta\omega_m,$$

$$\epsilon_a = kB(r) = kRe \Sigma_{m=1}^M (-i\omega_m) E^b(r, \omega_m) \cdot E^{as}(r, \omega_m) \Delta\omega_m. \quad (22)$$

In time domain the calculation of cross power spectrums $A(r)$ and $B(r)$ can be reduced to cross correlation between the background and backscattering anomalous fields and between time derivative of the background field and backscattering field:

$$A(r) \approx \int_T E^b(r, t) \cdot E^{as}(r, -t) dt, \quad (23)$$

$$B(r) \approx \int_T \frac{\partial E^b(r, t)}{\partial t} \cdot E^{as}(r, -t) dt.$$

where T is time interval. The last formulae can be computed numerically by the following expressions:

$$A(r) \approx \sum_{l=1}^L E^b(r, t_l) \cdot E^{as}(r, -t_l) \Delta t_l, \quad (24)$$

-continued $$B(r) \approx \sum_{l=1}^{L} \frac{\partial E^b}{\partial t}(r, t_l) \cdot E^{as}(r, t_l) \Delta t_l.$$

The volume images of anomalous conductivity $\sigma_a(r)$ and of anomalous permittivity $\epsilon_a(r)$ are constructed on the basis of cross power spectra A(r) and B(r) by formula (12).

EXAMPLE 3

It is possible to improve the resolution of imaging by repeating the steps of the previous examples iteratively. This procedure solves the inverse problem for determination of the material properties and location of the target.

The general iterative process can be described by the formula:

$$\tilde{\sigma}_{a(n+1)}(r) = \tilde{\sigma}_{a(n)}(r) + k_n A_n(r) - i\omega B_n(r) \quad (25)$$

where n=1, 2, 3, . . . , N; $k_1=k$; $A_1(r)=A(r)$, $B_1(r)=B(r)$; and $\tilde{\sigma}_{a(1)}(r)=\sigma_a(r)-i\omega kB(r)=kA(r)-i\omega kB(r)$.

The cross power spectra on the n-th iteration $A_n(r)$ an $dB_n(r)$ can be calculated by formulae, analogous to (1) and (11) in the frequency domain:

$$A_n(r)=Re\int_\Omega E_n^b(r, \omega) \cdot E_n^a(r, \omega)d\omega,$$

$$B_n(r)=Re\int_\Omega (-i\omega)E_n^b(r, \omega) \cdot E_n^b(r, \omega)d\omega, \quad (26)$$

where $E_n^b(r, \omega)$ is the corrected background field calculated by forward modeling for the geoelectrical model with the corrected background conductivity distribution $\tilde{\sigma}_{b(n)} = \tilde{\sigma}_{a(n)} + \tilde{\sigma}_{a(n)}$, and $E_n^s(r, \omega)$, is the corrected backscattering field of the corrected residual field $E^{\Delta n}$, which is the difference between the observed field and the corrected background field $E_n^b(r, \omega)$, found on the n-th iteration.

In the time domain, the functions $A_n(r)$ and $B_n(r)$ on the n-th iteration are determined by the cross correlation between corrected background and corrected backscattering fields according to the formulae:

$$A_n(r) = \int_T E_n^b(r, t) \cdot E_n^{a(r,-t)} dt \quad (27)$$

$$B_n(r) = \int_T \frac{\partial E_n^b(r, t)}{\partial t} \cdot E_n^{as}(r, -t) dt.$$

On every iteration, the same steps are applied:

Step 1. Calculating an updated (corrected) background field as electromagnetic response for the updated background medium with the complex conductivity $\tilde{\sigma}_{b(n)}(r)$, obtained on the previous iteration.

Step 2. Calculating the updated residual field between this response and observed field, and then calculating the updated backscattering field for the updated residual field by simulating illumination of the updated background medium with electric and magnetic currents equivalent to those of the updated residual field recorded at the location of the receivers.

Step 3. Constructing the updated volume images of anomalous conductivity $\tilde{\sigma}_{a(n)}(r)$ and of anomalous permittivity $\epsilon_{a(n)}(r)$ on the basis of updated [according to the formulae (26) and (27)] cross power spectra $A_n(r)$ and $B_n(r)$ $$\sigma_{a(n)}(r)=k_n A_n(r), \epsilon_{a(n)}(r)=k_n B_n(r) \quad (28)$$

where $k_n>0$ is a scale factor calculated using the line each for minimum of the energy functional:

$$\Phi(\tilde{\sigma}_b + \tilde{\sigma}_{a(n+1)}) = \Phi(\tilde{\sigma}_b + \tilde{\sigma}_{a(n)} + k_n A_n - i\omega k_n B_n) = \min. \quad (29)$$

The iterations can be terminated when the functional $\Phi(\tilde{\sigma}_b + \tilde{\sigma}_{a(n+1)})$ reaches the required accuracy level.

Thus, the computer of the system may be operated iteratively through the steps of: (1) updating the background field obtained in a previous iteration by adding the volume image constructed during that previous iteration; (2) repeating at least the steps of the method involving measuring (either empirically or numerically) the scattered electromagnetic field with the receivers through obtaining a next generation iteration of a volume image; and (3) repeating steps (1) and (2) until the updated background medium approximates the updated volume image. Regularization procedures such as described in M. S. Zhdanov and G. Hursan, 2000, 3-D electromagnetic inversion based on quasi-analytical approximation, Inverse Problems, 16, 1297–1322 can be used in the iterative process to generate a stable and resolved image.

Reference in this disclosure to details of specific embodiments is not intended to limit the scope of the appended claims.

INDUSTRIAL APPLICABILITY

The method can be applied in a variety of contexts. For example, internal defects in metal or concrete constructions can be located and imaged. The method is also useful for locating and imaging underground geological structures in connection with exploration for mineral, hydrocarbons and groundwater and in connection with environmental clean up activities. A particularly promising application involves imaging internal structures of living animals, notably the internal organs of the human body. To examine a diseased liver, for example, a normal body may serve as a reference model from which to derive a background field. To examine a diseased bone, such as in the case of osteoporosis, a normal bone may serve as a reference model.

Application for Breast Cancer, Osteoporosis, and Other Diseases Screening

Studies have shown that diseased human body parts often possess an abnormal level of conductivity and/or dielectric permittivity. For example, Colton and Monk (1995) reported that the presence of leukemia in bone marrow causes an increase in the dielectric permittivity and a decrease in the conductivity of the marrow. By determining the electrical conductivity and dielectric permittivity of a patient's tissues, broad band electromagnetic imaging methods can be used to detect diseased tissues, such as malignant tumor, and to differentiate diseased tissues from normal tissues.

Broad band electromagnetic imaging methods have many advantages over traditional examination methods such as X-ray. For example, broad band electromagnetic imaging methods are safer because they use electromagnetic energy that is non-ionizing. Broad band electromagnetic imaging methods are also safer because they use low-frequency energy typically in the 1–100 MHz range, lower than X-ray energy that is typically in the 1 GHz range. Broad band electromagnetic imaging methods are also patient-friendly, because they do not necessarily require contact with a patient's body or compression of a patient's body.

One of the uses of broad band electromagnetic imaging methods in the medical field is breast cancer screening. By measuring the conductivity and dielectric permittivity of a patient's breasts, malignant tissue whose conductivity and/or dielectric permittivity are different from normal tissue can be detected. Broad band electromagnetic imaging methods can also be used in combination with other screening methods such as palpation or mammography to increase cancer-detection rate and to reduce false-positive rate.

In addition to breast cancer screening, broad band electromagnetic imaging methods can also be used to examine other body parts for other diseases, including animal body parts for diseases. For example, broad band electromagnetic imaging methods can be used for osteoporosis screening, to detect abnormal bones with density loss. By producing a 3-D image of conductivity and permittivity of bones, the described methods can detect abnormal bones and provide valuable information to medical doctors and patients. The frequency of the electromagnetic energy used in the examination may be adjusted to allow desired penetration and contrast sensitivity of the body part examined. The frequency may be adjusted based on desired examination depth and density.

Application for Nondestructive Testing

Broad band electromagnetic imaging methods can also be used for nondestructive testing of technical structures. Technical structures such as walls, internal structural supports of buildings, aircraft structures and automobile structures are traditionally tested using eddy current testing, ultrasound testing, and other methods. Broad band electromagnetic imaging methods can be used to produce a 3-D image of conductivity and permittivity distribution within the examined structure. Compared to eddy current testing, which can only examine conductive structures, broad band electromagnetic methods can also examine non-conductive structures. Broad band electromagnetic methods also provide more detailed quantitative information on conductivity and permittivity distribution within the examined structure.

Embodiments of a Medical Test Device

One embodiment of a test device includes a galvanic transmitter and a galvanic receiver. The galvanic transmitter includes a pair of current electrodes that are connected to the examined medium. A current of electricity is sent from the current electrodes to the examined medium. The galvanic receiver also includes a pair of current electrodes that are connected to the examined medium. The galvanic receiver measures the electric potential difference between its two current electrodes connected to the examined medium.

Another embodiment of a test device includes an inductive transmitter and an inductive receiver. The transmitter includes a solenoid induction coil. When electricity is sent to the coil, it induces a transient electromagnetic field that penetrates through the examined medium. The receiver also includes an induction coil. The receiver coil measures the electromagnetic field caused by electromagnetic response from the examined medium. The analog signals measured by the receiver are converted by a support electronics module into digital signals. One embodiment of a support electronics module is an analog-to-digital converter. The converted digital signals are then used by a computer to produce images of conductivity and/or dielectric permittivity. Compared to galvanic transmitters and receivers, inductive transmitters and receivers have the advantage of not requiring physical contact with the examined medium.

Figure 7A:
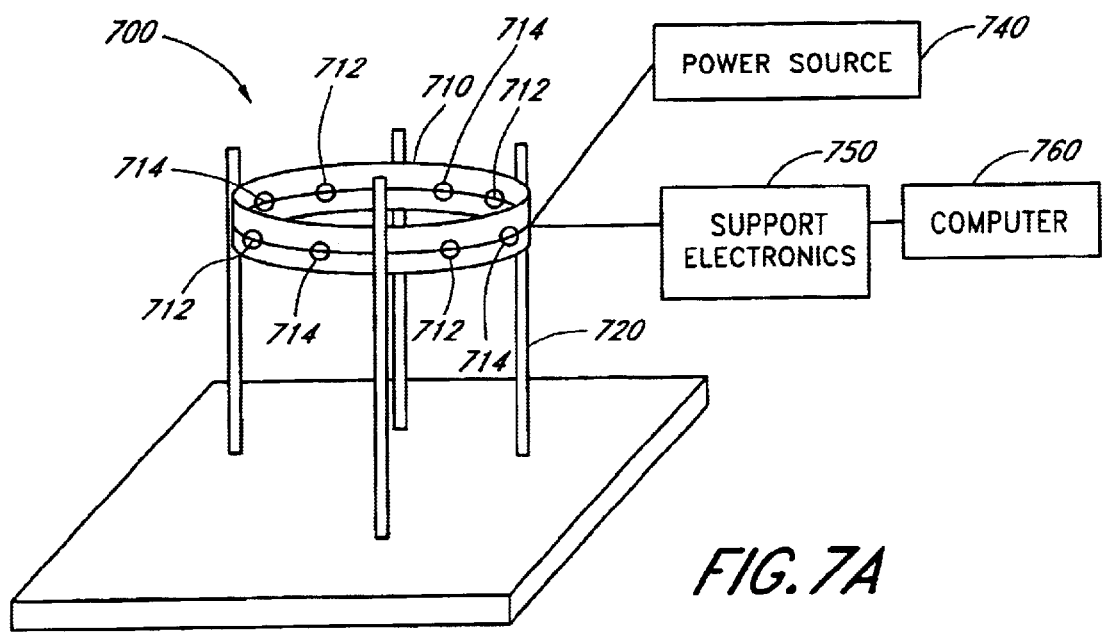
FIG. 7A is a diagram illustrating one embodiment of a medical test device.
Figure 7B:
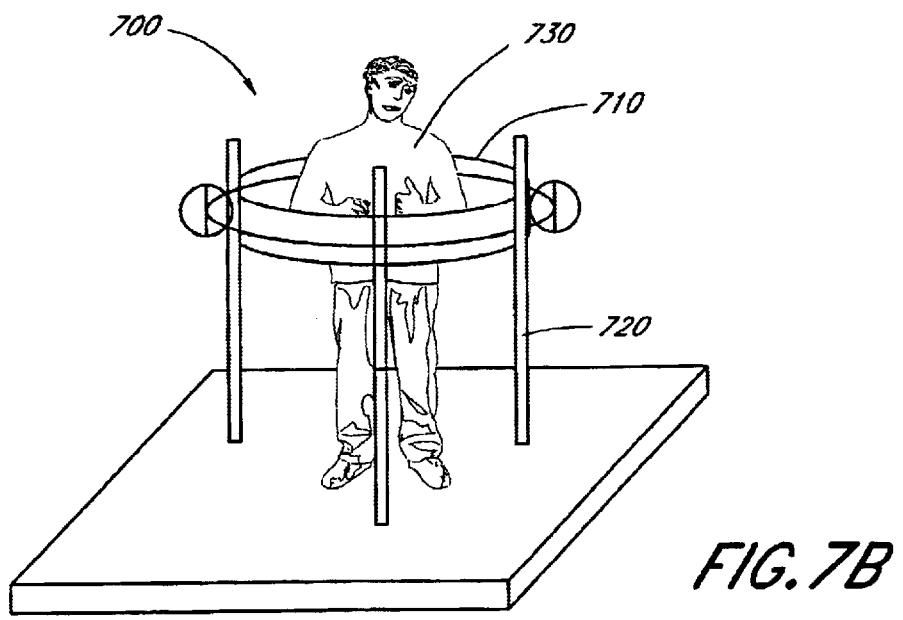
FIG. 7B is a diagram illustrating one embodiment of the medical test device as applied to a patient.

FIG. 7A and FIG. 7B illustrate one embodiment of a test device 700. As shown in FIG. 7A, one or more transmitter coils 712 and one or more receiver coils 714 are placed along a ring 710. The ring 710 is placed horizontally and supported by vertical posts 720. In one implementation illustrated in FIG. 7B, the ring 710 has a diameter (such as 1–2 meters) sufficient for a patient 730 to stand in. In another implementation, the ring 710 has a diameter (such as 10–20 centimeters) sufficient for a patient to insert a body part such as a hand, a foot, or a breast into the ring 710. In one implementation, the ring 710 can be moved up and down along the vertical posts 720, so that the ring 710 can be placed to examine multiple cross sections of the patient's body 730. For example, the ring 710 can be slidingly connected to the vertical posts 720, or connected to the vertical posts 720 using holes and clamps, so that the height of the ring 710 can be adjusted. In another implementation, the vertical posts 720 are adjustable in height (for example made of telescoping tubes), therefore making the ring 710 adjustable in height.

Referring back to FIG. 7A, the transmitter coils 712 are connected through the ring 710 to a power source 740. The receiver coils 714 are connected through the ring 710 to a support electronics module 750, which is connected to a computer 760. In one embodiment illustrated in FIG. 7A, four transmitter coils 712 and four receiver coils 714 are distributed along the ring 710. In another embodiment, eight transmitter coils 712 and sixteen receiver coils 714 are distributed along the ring 710.

During operation, electricity is sent from the power source 740 to the transmitter coils 712. The transmitter coils 712 illuminate the examined medium with electromagnetic field, to be recorded by the receiver coils 714. In one embodiment, the intensity of the signals has an approximate dynamic range between 100 dB to 140 dB (decibel). In one embodiment, the signal frequency is between approximately 1 megahertz and approximately 10 megahertz. In another embodiment, the signal frequency is between approximately 1 megahertz and approximately 100 megahertz. The electromagnetic signals generated by the transmitter coils 712 are called primary signals. The primary signals interact with the examined target inside the ring 710 and result in a scattered electromagnetic field of secondary signals. The receiver coils 714 record the primary signals and secondary signals and send the recorded signals to the support electronics module 750 for processing. The support electronics module 750 converts the received analog signals into digital signals, and filters out the primary signals. The remaining secondary digital signals are processed by the computer 760 to produce images of conductivity and/or dielectric permittivity of the examined area. In one implementation, the ring 710 is moved up and down the vertical posts 720, an examination is performed for every ring location on the vertical posts 720, in order to generate a plurality of cross sections of conductivity and dielectric permittivity data for the patient body 730.

In one embodiment, each of the coils can serve as both a transmitter coil and a receiver coil. For example, the coil 712 first serves as a transmitter, receives electricity from the power source 740 and illuminates the examined medium with electromagnetic field. Since electromagnetic field can at least partially remain for a short period of time, the coil 712 can then serve as a receiver and record the electromagnetic field.

Another embodiment of a test device (not shown) is a hand held device that includes a transmitter and a receiver. The hand held device is placed on or in proximity to a part of a patient body. The hand held device is connected to a support electronics module, which is connected to a computer. After conductivity and/or permittivity data of the part of the patient body is obtained, the hand held device can be placed on or in proximity to another part of the patient body. By moving the hand held device along a patient body surface, maps of conductivity and/or permittivity can be obtained.

Yet another embodiment of a test device (not shown) is a scanning chamber in a form similar to a MRI scan chamber. A patient is placed inside the chamber. One of more transmitters and one or more receivers placed on the interior wall of the chamber then respectively produce and record electromagnetic fields. The recorded analog signals are converted by a support electronics module to digital signals. The digital signals are then processed by a computer to produce images of conductivity and/or permittivity.

Still another embodiment of a test device (not shown) is a scanning bed with one or more adjustable straps. One or more transmitters and one or more receivers are placed on each of the straps. After a patient is placed on the bed, the straps are placed on the part of the patient body that is to be examined. Transmitters and receivers then respectively produce and record electromagnetic signals. In one embodiment, the straps can be removed from the bed and reattached to the bed, to be placed on another part of the patient body.

Each embodiment of the test device is connected to a support electronics module, which is connected by wire or wirelessly to a computer. After the receivers record a scattered electromagnetic field, the analog signals of the field is converted by the support electronics module to digital signals. The computer receives the digital signals of the scattered electromagnetic field from the support electronics module, creates a simulated homogeneous background field that represents the examined background medium (such as the patient's body) without the examined target (such as the patient's breast, liver, bone, etc.), creates a simulated backscatttering anomalous field that represents an electromagnetic field obtainable by transmitting the scattered electromagnetic field from the receivers to illuminate the background medium, and produces a volume image of the conductivity and/or dielectric permittivity of the examined target. In one embodiment, the computer produces the volume image by calculating cross power spectra of the background field and the backscattering field. In another embodiment, the computer produces the volume image by calculating cross correlation functions between the background field and the backscattering field.

In yet another embodiment, the computer produces the volume image iteratively by:

Calculating an updated (corrected) background field as electromagnetic response for the updated background medium with the complex conductivity, obtained on the previous iteration;

Calculating the updated residual field between this response and observed field, and calculating the updated backscattering field for the updated residual field by simulating illumination of the updated background medium with electric and magnetic currents equivalent to those of the updated residual field recorded at the location of the receivers; and Constructing the updated volume images of anomalous conductivity $\tilde{\sigma}_{a(n)}(r)$ and of anomalous permittivity $\epsilon_{a(n)}(r)$ on the basis of updated cross power spectrum or cross correlation functions between said background field and said updated backscattering field, using regularization procedures.

CONCLUSION

The following articles are incorporated by reference in their entirety: M. S. Zhdanov, S. Fang and G. Hursan, 2000, Electromagnetic inversion using quasi-linear approximation, Geophysics, 65, No. 5, 1501–1513; M. S. Zhdanov and G. Hursan, 2000, 3-D electromagnetic inversion based on quasi-analytical approximation, Inverse Problems, 16, 1297–1322.

The invention may be embodied in other specific forms without departing from the essential characteristics as described herein. The embodiments described above are to be considered in all respects as illustrative only and not restrictive in any manner. The scope of the invention is indicated by the following claims and their equivalents rather than by the foregoing description.

What is claimed is:

1. A method for imaging an anomalous region located within a nontransparent medium of an organism, said method comprising the steps of:
   a. placing one or more electromagnetic transmitters in transmission contact with said medium;
   b. placing one or more electromagnetic receivers at receiving positions with respect to said medium;
   c. operating said transmitters to generate a broad band electromagnetic field, comprising a frequency domain and/or time domain electromagnetic field, whereby said generated electromagnetic field propagates through said medium to interact with said anomalous region, resulting in a scattered electromagnetic field;
   d. measuring said scattered electromagnetic field with said receivers;
   e. obtaining a background field $\{E^b, H^b\}$ representative of a background medium equivalent to said medium without the presence of said anomalous region;
   f. obtaining a backscattering anomalous field $\{E^{as}, H^{as}\}$ equivalent to that obtainable by illuminating said background medium with said scattered electromagnetic field transmitted from the receiving positions of said receivers; and
   g. producing a broad band holographic image of said anomalous region by calculating cross power spectra of said background and said backscattering fields, or calculating cross correlation functions between said background and said backscattering fields.

2. The method of claim 1, wherein said produced image of said anomalous region identifies a medical condition of said anomalous region.

3. The method of claim 1, wherein said produced image of said anomalous region identifies an abnormal portion of said anomalous region.

4. The method of claim 1, wherein operating said transmitters to generate a broad band electromagnetic field comprises operating said transmitters to generate a broad band electromagnetic field with a frequency between approximately one megahertz and approximately ten megahertz.

5. The method of claim 1, wherein operating said transmitters to generate a broad band electromagnetic field comprises operating said transmitters to generate a broad band electromagnetic field with a frequency between approximately ten megahertz and approximately one hundred megahertz.

6. The method of claim 1, wherein operating said transmitters to generate a broad band electromagnetic field comprises operating said transmitters to generate a broad band electromagnetic field with a frequency of between approximately one megahertz and approximately one hundred megahertz.

7. The method of claim 1, wherein said broad band electromagnetic field comprises a portion of EM spectrum, wherein propagation of said portion is characterized by diffusion phenomena.

8. The method of claim 1, wherein said broad band electromagnetic field comprises a portion of EM spectrum, wherein propagation of said portion is characterized by a combination of diffusion phenomena and wave phenomena.

9. A system of imaging a body part of a human or animal, comprising:

an imaging ring including one or more transmitter coils and one or more receiver coils, said imaging ring configured to accommodate said body part inside said imaging ring, said transmitter coils configured to generate a broad band electromagnetic field comprising a frequency domain and/or time domain electromagnetic field, whereby said generated electromagnetic field propagates through said human or animal and interacts with said body part to result in a scattered electromagnetic field, said receiver coils configured to record said scattered electromagnetic field; and a computer configured to simulate a background field representing a hypothetical electromagnetic field of said human or animal without said body part, to compute a backscattering field representing another hypothetical electromagnetic field obtainable by transmitting said scattered electromagnetic field from said receivers, and to produce a volume image of electric conductivity and/or dielectric permittivity of said body part.

10. The system of claim 9, wherein the computer is configured to produce said volume image by calculating cross power spectra of said background field and said backscattering field.

11. The system of claim 9, wherein the computer is configured to produce said volume image by calculating cross correlation functions between said background field and said backscattering field.

12. The system of claim 9, further comprising one or more support posts connected to said imaging ring and configured to support said imaging ring.

13. The system of claim 12, wherein said support posts are adjustable in height.

14. The system of claim 12, wherein said imaging ring is adjustable in height along said support posts.

15. The system of claim 9, wherein the computer is configured to produce said volume image iteratively by:

calculating an updated (corrected) background field as electromagnetic response for the updated background medium with the complex conductivity, obtained on the previous iteration;

calculating the updated residual field between this response and observed field;

calculating the updated backscattering field for the updated residual field by simulating illumination of the updated background medium with electric and magnetic currents equivalent to those of the updated residual field recorded at the location of the receivers; and constructing the updated volume images of anomalous conductivity $\tilde{\sigma}a(n)(r)$ and of anomalous permittivity $\epsilon_{a(n)}(r)$ on the basis of updated cross power spectrum or cross correlation functions between said background field and said updated backscattering field, using regularization procedures.

16. The system of claim 9, further comprising a converter configured to receive analog signals of said scattered electromagnetic field from said receiver coils, to convert said received analog signals into digital signals of said scattered electromagnetic field, and to transmit said digital signals to said computer.

17. The system of claim 9, wherein said receiver coils are further configured to record said generated electromagnetic field, said system further comprising a filter configured to receive said generated electromagnetic filed and said scattered electromagnetic field from said receiver coils, to filter said generated electromagnetic field from said scattered electromagnetic field, and to transmit said scattered electromagnetic field to said computer.

* * * * *

UNITED STATES PATENT AND TRADEMARK OFFICE
CERTIFICATE OF CORRECTION

PATENT NO. : 6,876,878 B2
DATED : April 5, 2005
INVENTOR(S) : Michael S. Zhdanov It is certified that error appears in the above-identified patent and that said Letters Patent is hereby corrected as shown below:

Title page,
Item [74], *Attorney, Agent or Firm*, after "Martens" delete ",".

Column 18,
Line 21, delete " $\tilde{\sigma}a(n)(r)$ " and insert -- " $\tilde{\sigma}_{a(n)}(r)$ " --.

Line 36, after "electromagnetic" delete "filed" and insert -- field --.

Signed and Sealed this

Thirty-first Day of January, 2006

JON W. DUDAS
*Director of the United States Patent and Trademark Office*

UNITED STATES PATENT AND TRADEMARK OFFICE
CERTIFICATE OF CORRECTION

PATENT NO.        : 6,876,878 B2                                                    Page 1 of 1
APPLICATION NO. : 09/876262
DATED             : April 5, 2005
INVENTOR(S)       : Michael S. Zhdanov It is certified that error appears in the above-identified patent and that said Letters Patent is hereby corrected as shown below:

Cover Page, line 63 and Page 1, line 5, of the Specification - The priority claim states that the Patent is a "Continuation of application No. 09/214,217," and should state that the Patent is a "Continuation-In-Part of application No. 09/214,217," as claimed in the original Specification, as acknowledged in the Notice of Allowability, page 2, mailed on June 12, 2003, and as reflected in paragraph [0001] of the publication (US Publication No. 2002/0062074) on May 23, 2002.

Signed and Sealed this

Seventh Day of July, 2009

JOHN DOLL
*Acting Director of the United States Patent and Trademark Office*